US010792023B2

(12) United States Patent
Prior

(10) Patent No.: US 10,792,023 B2
(45) Date of Patent: Oct. 6, 2020

(54) SHAFT DRIVEN MECHANISM FOR ARTICULATING TISSUE SPECIMEN RETRIEVAL DEVICE

(71) Applicant: Covidien LP, Mansfield, MA (US)

(72) Inventor: Scott J. Prior, Shelton, CT (US)

(73) Assignee: Covidien LP, Mansfield, MA (US)

( * ) Notice: Subject to any disclaimer, the term of this patent is extended or adjusted under 35 U.S.C. 154(b) by 211 days.

(21) Appl. No.: 16/001,061

(22) Filed: Jun. 6, 2018

(65) Prior Publication Data
US 2019/0374212 A1    Dec. 12, 2019

(51) Int. Cl.
*A61B 17/00* (2006.01)
*A61B 17/221* (2006.01)

(52) U.S. Cl.
CPC ...... *A61B 17/00234* (2013.01); *A61B 17/221* (2013.01); *A61B 2017/00287* (2013.01); *A61B 2017/00867* (2013.01)

(58) Field of Classification Search
CPC ........ A61B 2017/00287; A61B 17/221; A61B 2017/00367; A61B 2017/2212; A61B 2017/2215; A61B 2017/2217; A61B 2017/2939; A61B 2017/2927; A61B 2017/2908; A61B 1/008; A61M 25/0133; A61M 25/0147
See application file for complete search history.

(56) References Cited

U.S. PATENT DOCUMENTS

| 5,501,654 | A | * | 3/1996 | Failla ............... A61B 17/0218 600/204 |
| 5,643,283 | A | | 7/1997 | Younker |
| 6,059,793 | A | | 5/2000 | Pagedas |
| 6,156,055 | A | | 12/2000 | Ravenscroft |
| 6,162,209 | A | | 12/2000 | Gobron et al. |
| 6,171,317 | B1 | | 1/2001 | Jackson et al. |
| 6,206,889 | B1 | | 3/2001 | Bennardo |
| 6,224,612 | B1 | | 5/2001 | Bates et al. |
| 6,228,023 | B1 | * | 5/2001 | Zaslavsky ............ A61B 17/221 600/204 |

(Continued)

FOREIGN PATENT DOCUMENTS

WO    2004002334 A1    1/2004
WO    2014158880 A1    10/2014

Primary Examiner — Christopher L Templeton
Assistant Examiner — Andrew P. Restaino
(74) Attorney, Agent, or Firm — Carter, DeLuca & Farrell LLP

(57) ABSTRACT

A tissue specimen retrieval device includes a housing having an outer shaft that extends distally therefrom. An end effector assembly is included that extends distally from the outer shaft in a deployed position. A first actuator is operably associated with the housing and actuatable to deploy and retract the end effector assembly. A drive shaft operably couples to the first actuator and includes a link disposed at a distal end thereof that operably couples to the end effector assembly. The drive shaft is movable via actuation of the first actuator from a first position wherein the end effector assembly and link are retracted within the outer shaft to a second position wherein the end effector assembly and link are fully exposed from the outer shaft. The link includes a biasing member that, once the link is fully exposed, articulates the end effector assembly to a position to engage tissue.

11 Claims, 5 Drawing Sheets

(56) References Cited

U.S. PATENT DOCUMENTS

| | | |
|---|---|---|
| 6,228,095 B1 | 5/2001 | Dennis |
| 6,248,113 B1 | 6/2001 | Fina |
| 6,258,102 B1 | 7/2001 | Pagedas |
| 6,264,663 B1 | 7/2001 | Cano |
| 6,270,505 B1 | 8/2001 | Yoshida et al. |
| 6,280,451 B1 | 8/2001 | Bates et al. |
| 6,344,026 B1 | 2/2002 | Burbank et al. |
| 6,350,266 B1 | 2/2002 | White et al. |
| 6,350,267 B1 | 2/2002 | Stefanchik |
| 6,358,198 B1 | 3/2002 | Levin et al. |
| 6,368,328 B1 | 4/2002 | Chu et al. |
| 6,383,195 B1 | 5/2002 | Richard |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,447,523 B1 | 9/2002 | Middleman et al. |
| 6,530,923 B1 | 3/2003 | Dubrul et al. |
| 6,537,273 B1 | 3/2003 | Sosiak et al. |
| 6,752,822 B2 | 6/2004 | Jespersen |
| 6,805,699 B2 | 10/2004 | Shimm |
| 6,951,533 B2 | 10/2005 | Foley |
| 6,986,774 B2 | 1/2006 | Middleman et al. |
| 7,037,275 B1 | 5/2006 | Marshall et al. |
| 7,052,501 B2 | 5/2006 | McGuckin, Jr. |
| 7,087,062 B2 | 8/2006 | Dhindsa |
| 7,101,379 B2 | 9/2006 | Gregory, Jr. et al. |
| 7,101,380 B2 | 9/2006 | Khachin et al. |
| 7,112,172 B2 | 9/2006 | Orban, III et al. |
| 7,115,125 B2 | 10/2006 | Nakao et al. |
| 7,144,400 B2 | 12/2006 | Byrum et al. |
| 7,169,154 B1 | 1/2007 | Que et al. |
| 7,229,418 B2 | 6/2007 | Burbank et al. |
| 7,285,126 B2 | 10/2007 | Sepetka et al. |
| 7,316,692 B2 | 1/2008 | Huffmaster |
| 7,357,801 B2 | 4/2008 | Burbank et al. |
| 7,534,252 B2 | 5/2009 | Sepetka et al. |
| 7,547,310 B2 | 6/2009 | Whitfield |
| 7,615,013 B2 | 11/2009 | Clifford et al. |
| 7,618,437 B2 | 11/2009 | Nakao |
| 7,645,283 B2 | 1/2010 | Reynolds et al. |
| 7,670,346 B2 | 3/2010 | Whitfield |
| 7,678,118 B2 | 3/2010 | Bates et al. |
| 7,722,626 B2 | 5/2010 | Middleman et al. |
| 7,727,227 B2 | 6/2010 | Teague et al. |
| 7,731,722 B2 | 6/2010 | Lavelle et al. |
| 7,731,723 B2 | 6/2010 | Kear et al. |
| 7,762,959 B2 | 7/2010 | Bilsbury |
| 7,762,960 B2 | 7/2010 | Timberlake et al. |
| 7,875,038 B2 | 1/2011 | Que et al. |
| 7,892,242 B2 | 2/2011 | Goldstein |
| 7,914,540 B2 | 3/2011 | Schwartz et al. |
| 7,918,860 B2 | 4/2011 | Leslie et al. |
| 7,955,292 B2 | 6/2011 | Leroy et al. |
| 8,057,485 B2 | 11/2011 | Hollis et al. |
| 8,075,567 B2 | 12/2011 | Taylor et al. |
| 8,118,816 B2 | 2/2012 | Teague |
| 8,152,820 B2 | 4/2012 | Mohamed et al. |
| 8,172,772 B2 | 5/2012 | Zwolinski et al. |
| 8,211,115 B2 | 7/2012 | Cheng et al. |
| 8,282,572 B2 | 10/2012 | Bilsbury |
| 8,337,510 B2 | 12/2012 | Rieber et al. |
| 8,348,827 B2 | 1/2013 | Zwolinski |
| 8,409,216 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,486,087 B2 | 7/2013 | Fleming |
| 8,512,351 B2 | 8/2013 | Teague |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,956,370 B2 | 2/2015 | Taylor et al. |
| 8,968,329 B2 | 3/2015 | Cabrera |
| 8,986,321 B2 | 3/2015 | Parihar et al. |
| 9,005,215 B2 | 4/2015 | Grover et al. |
| 9,017,328 B2 | 4/2015 | Bahney |
| 9,017,340 B2 | 4/2015 | Davis |
| 9,033,995 B2 | 5/2015 | Taylor et al. |
| 9,084,588 B2 | 7/2015 | Farascioni |
| 9,101,342 B2 | 8/2015 | Saleh |
| 9,113,848 B2 | 8/2015 | Fleming et al. |
| 9,113,849 B2 | 8/2015 | Davis |
| 9,308,008 B2 | 4/2016 | Duncan et al. |
| 9,364,201 B2 | 6/2016 | Orban, III |
| 9,364,202 B2 | 6/2016 | Menn et al. |
| 9,370,341 B2 | 6/2016 | Ceniccola et al. |
| 9,370,378 B2 | 6/2016 | O'Prey et al. |
| 9,375,224 B2 | 6/2016 | Jansen |
| 9,414,817 B2 | 8/2016 | Taylor et al. |
| 9,468,452 B2 | 10/2016 | Menn et al. |
| 9,486,188 B2 | 11/2016 | Secrest et al. |
| 9,522,034 B2 | 12/2016 | Johnson et al. |
| 9,549,747 B2 | 1/2017 | Carlson |
| 9,579,115 B2 | 2/2017 | Kahle et al. |
| 9,592,067 B2 | 3/2017 | Hartoumbekis |
| 9,622,730 B2 | 4/2017 | Farascioni |
| 9,629,618 B2 | 4/2017 | Davis et al. |
| 9,642,638 B1 | 5/2017 | Carrier |
| 9,655,644 B2 | 5/2017 | Collins |
| 9,730,716 B2 | 8/2017 | Secrest et al. |
| 9,789,268 B2 | 10/2017 | Hart et al. |
| 9,808,228 B2 | 11/2017 | Kondrup et al. |
| 9,826,997 B2 | 11/2017 | Cherry et al. |
| 9,867,600 B2 | 1/2018 | Parihar et al. |
| 9,877,893 B2 | 1/2018 | Taylor et al. |
| 2012/0083796 A1* | 4/2012 | Grover ............ A61B 17/00234 606/114 |
| 2017/0020500 A1* | 1/2017 | Taylor ............ A61B 17/00234 |

* cited by examiner

SHAFT DRIVEN MECHANISM FOR ARTICULATING TISSUE SPECIMEN RETRIEVAL DEVICE

BACKGROUND

Technical Field

The present disclosure relates to tissue specimen retrieval from an internal body cavity and, more particularly, to articulation mechanisms for tissue specimen retrieval devices and tissue specimen retrieval devices incorporating the same to facilitate retrieval of a tissue specimen from the internal body cavity.

Background of Related Art

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total retrieval of a tissue specimen from an internal body cavity. However, the restricted access provided by minimally-invasive openings (natural passageways and/or surgically created openings) presents challenges with respect to maneuverability and visualization. The restricted access also presents challenges when the tissue specimen is required to be removed. As such, a tissue specimen that is deemed too large for intact retrieval may be broken down into a plurality of smaller pieces to facilitate retrieval from the internal body cavity.

During a hysterectomy or myomectomy the tissue specimen to be removed can contain occult malignancies, and the size of the specimen can be extremely large (size of a melon). Due to the size of the specimen, a traditional specimen bag may be inadequate due to the size of the bag. In addition, the port location and limited room for mobility of the deployment shaft within the cavity can inhibit the ideal angle to reach and load the large specimen. Therefore, articulation of the bag opening may significantly improve the positioning and ease of use for loading the tissue specimen.

Due to the low position of the vaginal canal, a straight-shafted instrument makes it difficult for the surgeon to achieve the proper elevation to contain the tissue specimen, and very difficult with the specimen bag opening being oriented in a parallel fashion with respect to the cavity. As a result, there exists a need for an articulated tissue specimen retrieval system.

SUMMARY

The present disclosure provides articulation mechanisms for tissue specimen retrieval devices to facilitate retrieval of the tissue specimen from an internal body cavity. These and other aspects and features of the present disclosure are detailed below. As used herein, the term "distal" refers to the portion that is described which is further from a user, while the term "proximal" refers to the portion that is being described which is closer to a user. Further, any or all of the aspects and features described herein, to the extent consistent, may be used in conjunction with any or all of the other aspects and features described herein.

Provided in accordance with aspects of the present disclosure is a tissue specimen retrieval device that includes a housing having an outer shaft that extends distally therefrom and that defines a longitudinal axis. An end effector assembly is included that extends distally from the outer shaft in a deployed position of the end effector assembly. A first actuator is operably associated with the housing and actuatable to deploy and retract the end effector assembly. A drive shaft operably couples to the first actuator and includes a link disposed at a distal end thereof that operably couples to the end effector assembly. The drive shaft is movable via actuation of the first actuator from a first position wherein the end effector assembly and link are retracted within the outer shaft to a second position wherein the end effector assembly and link are fully exposed from the outer shaft. The link includes a biasing member that, once the link is fully exposed, articulates the end effector assembly to a position to engage tissue.

In aspects according to the present disclosure, the drive shaft is movable to an intermediate position between the first and second positions wherein the end effector assembly is fully exposed from the outer shaft while the link remains at least partially disposed within the outer shaft. When disposed in the intermediate position, the exposed end effector assembly remains parallel to the longitudinal axis of the outer shaft. In other aspects according other present disclosure, the tissue specimen retrieval device further includes a second actuator operably coupled to the drive shaft, and wherein the first actuator actuates the drive shaft to move between the first position and the intermediate position to expose the end effector assembly and the second actuator actuates the drive shaft to move between the intermediate position and the second position to expose the link and articulate the end effector assembly.

In yet other aspects according to the present disclosure, the end effector assembly includes first and second arms configured to support a tissue specimen bag thereon. In further aspects according to the present disclosure, deployment of the end effector assembly automatically unfurls the tissue specimen bag. Still in other aspects, the first actuator is actuated in one direction from an un-actuated position to an actuated position and in an opposite direction from the actuated position back to the un-actuated position.

In accordance with additional aspects of the present disclosure, a tissue specimen retrieval device includes a housing having an outer shaft extending distally therefrom and defining a longitudinal axis. An end effector assembly extends distally from the outer shaft in a deployed position of the end effector assembly. A first actuator is operably associated with the housing and is actuatable to deploy and retract the end effector assembly. A drive shaft is operably coupled to the first actuator and includes a resilient portion having a bias. The resilient portion is disposed at a distal end of the drive shaft and operably couples to the end effector assembly. The drive shaft is movable via actuation of the first actuator from a first position wherein the end effector assembly and resilient portion are retracted within the outer shaft to a second position wherein the end effector assembly and resilient portion are fully exposed from the outer shaft. The bias of the resilient portion articulates the end effector assembly to a position to engage tissue.

In aspects according to the present disclosure, the drive shaft is movable to an intermediate position between the first and second positions wherein the end effector assembly is fully exposed from the outer shaft while the resilient portion remains at least partially disposed within the outer shaft.

When disposed in the intermediate position, the end effector assembly remains parallel to the longitudinal axis of the outer shaft.

In yet other aspects, the end effector assembly includes first and second arms configured to support a tissue specimen bag thereon. In still other aspects, deployment of the end effector assembly automatically unfurls the tissue specimen bag. In other aspects, the first actuator is actuated in one direction from an un-actuated position to an actuated position and in an opposite direction from the actuated position back to the un-actuated position.

In yet still other aspects according to the present disclosure, a second actuator is operably coupled to the drive shaft, and the first actuator actuates the drive shaft to move between the first position and the intermediate position to expose the end effector assembly and the second actuator actuates the drive shaft to move between the intermediate position and the second position to expose the resilient portion and articulate the end effector assembly.

In still other aspects, the resilient portion is made from a shape memory alloy. In aspects, the shape memory alloy is thermoelastic to transform from an austenite, straight configuration to a martensite, arcuate configuration upon a change in temperature. In other aspects, the shape memory alloy is stress-induced to transform from an austenite, straight configuration to a martensite, arcuate configuration when induced by stress.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
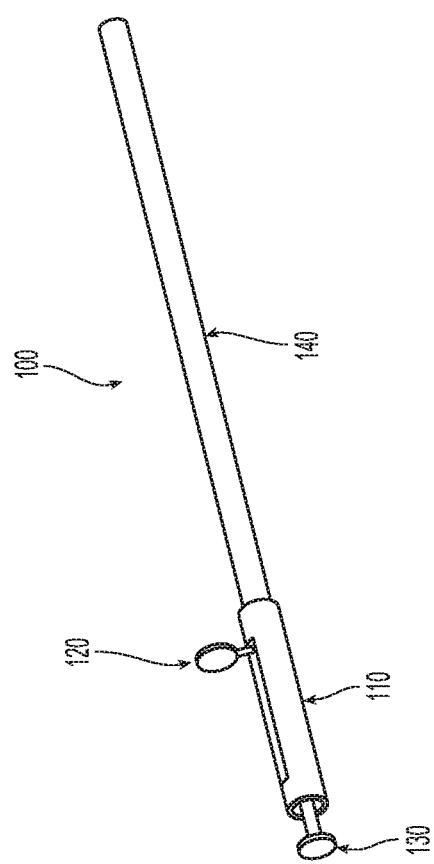
FIG. 1 is a side, perspective view of a tissue specimen retrieval device provided in accordance with aspects of the present disclosure, wherein an end effector assembly of the tissue specimen retrieval device is disposed in a retracted position.

The present disclosure provides articulation mechanisms for tissue specimen retrieval devices to facilitate retrieval of tissue from an internal body cavity.

Turning to FIGS. 1-5, a tissue specimen retrieval device provided in accordance with the present disclosure is shown generally identified by reference numeral 100. Tissue specimen retrieval device 100 includes a housing 110, first and second actuators 120, 130 operably associated with housing 110, an outer shaft 140 extending distally from housing 110, an end effector assembly 150 selectively deployable from the distal end of outer shaft 140, and a drive shaft 185 configured to enable selective articulation of end effector assembly 150 relative to outer shaft 140 in the deployed position of end effector assembly 150. Although the term "drive shaft" is used herein, any drive element which provides additional column strength may be used to serve the same purpose.

Housing 110, although illustrated as defining a generally tubular configuration, may define any suitable configuration to facilitate grasping and manipulating tissue specimen retrieval device 100 such as, for example, a pencil-grip configuration, a pistol-grip configuration, etc., and may include any suitable features to enhance ergonomics such as, for example, recesses, protrusions, textured surfaces, finger rings, etc.

First actuator 120 includes drive shaft 185 that is operably coupled to end effector assembly 150 to enable selective extension and retraction of end effector assembly 150 relative to housing 110 and, thus, outer shaft 140, to move end effector assembly 150 between a retracted position (FIG. 1) and a deployed position (FIG. 2) relative to outer shaft 140. Alternatively, first actuator 120 may be operably associated with housing 110 and coupled to outer shaft 140 to enable selective extension and retraction of outer shaft 140 relative to housing 110 and, thus, end effector assembly 150, to selectively move end effector assembly 150 between a retracted position (FIG. 1) and a deployed position (FIG. 2) relative to outer shaft 140 in response to actuation of first actuator 120. First actuator 120 may be configured as a sliding actuator slidable along housing 110, as illustrated, or may define any other suitable configuration such as, for example, a plunger actuator that is selectively manipulatable relative to housing 110 along a longitudinal axis of housing 110, a pivoting actuator pivotable relative to housing 110, etc.

A second actuator 130 may be operably associated with housing 110 and coupled to articulation portion 180, 280 (FIGS. 4 and 5) to enable selective articulation of end effector assembly 150 relative to outer shaft 140, once deployed from outer shaft 140, between an aligned position (FIG. 2) and an articulated position (FIG. 3), in response to actuation of second actuator 130. Second actuator 130 may be configured as a plunger actuator that is selectively manipulatable relative to housing 110 along a longitudinal axis of housing 110, as illustrated, or may define any other suitable configuration such as, for example, a pivoting actuator pivotable relative to housing 110, a sliding actuator slidable along housing 110, etc.

Figure 2:
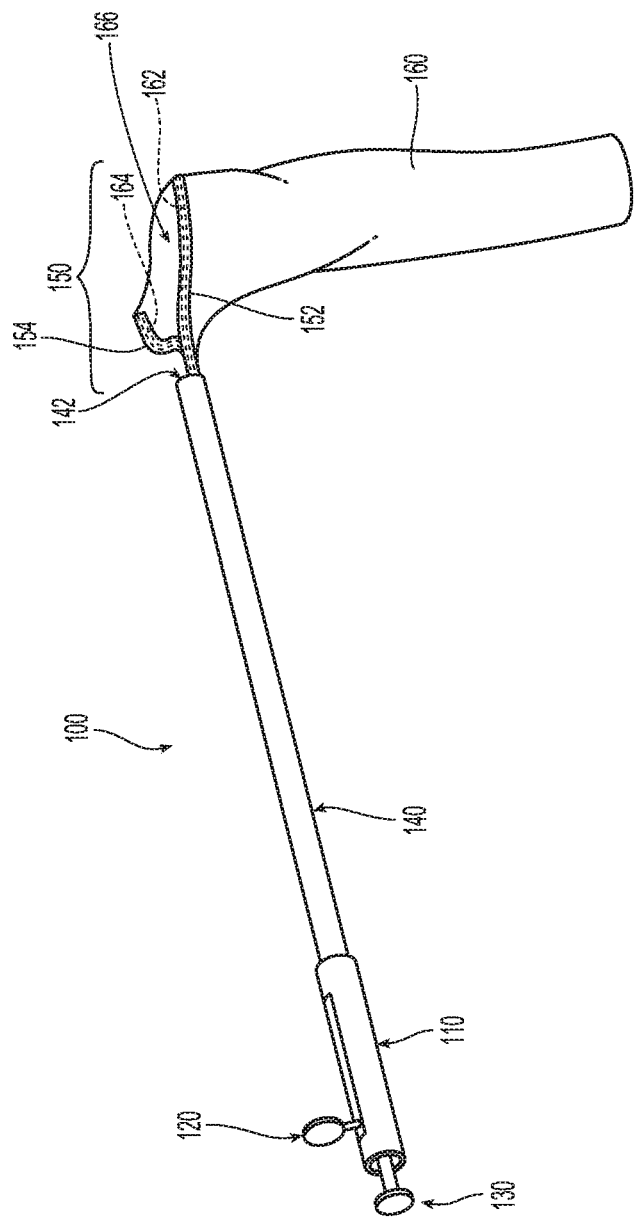
FIG. 2 is a side, perspective view of the tissue specimen retrieval device of FIG. 1, wherein the end effector assembly is disposed in a deployed, aligned position.
Figure 3:
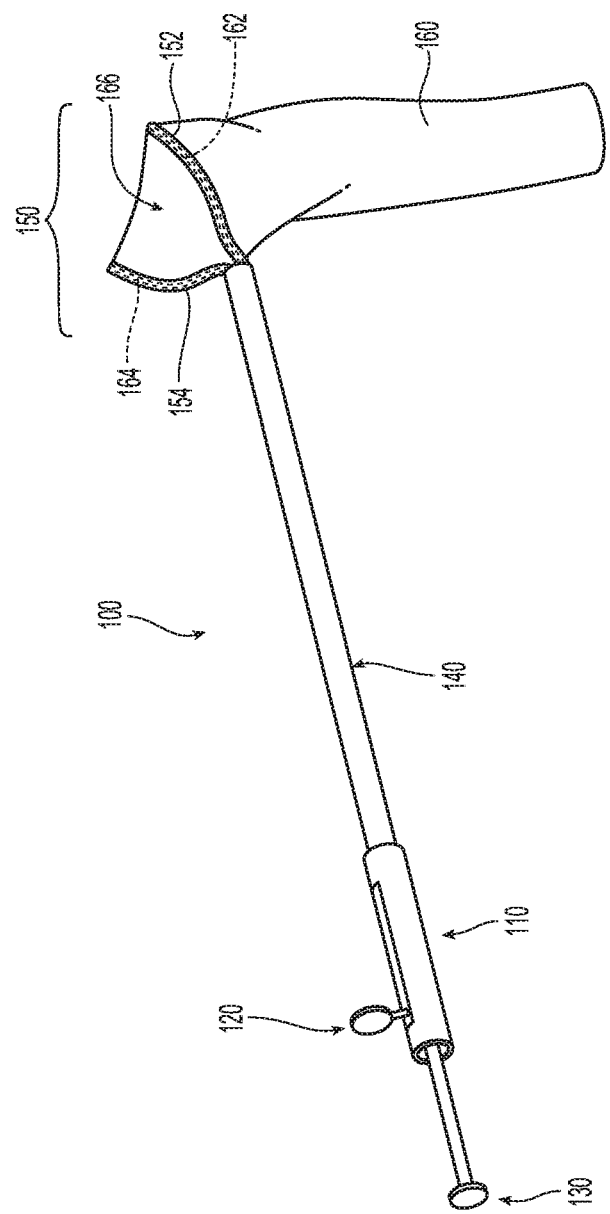
FIG. 3 is a side, perspective view of the tissue specimen retrieval device of FIG. 1, wherein the end effector assembly is disposed in a deployed, articulated position.
Figure 6:
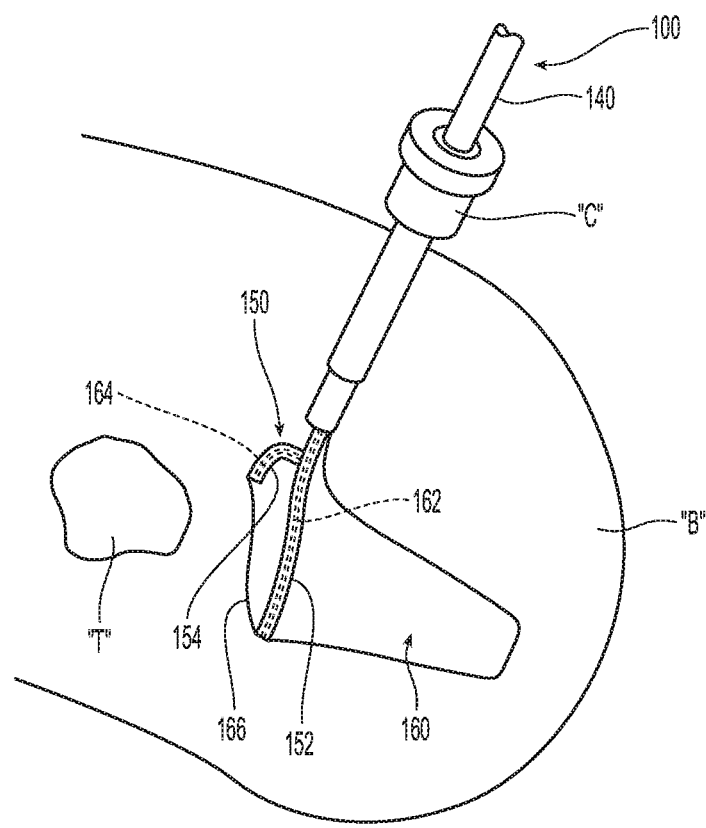
FIG. 6 is a perspective view of the tissue specimen retrieval device of FIG. 1 inserted through an access cannula into an internal body cavity for retrieval of a tissue specimen therefrom.

Continuing with reference to FIGS. 1-3, outer shaft 140 extends distally from housing 110, as noted above, and is configured for insertion through an access cannula "C" (FIG. 6) or natural passageway into an internal body cavity "B" (FIG. 6). Outer shaft 140 may be substantially rigid (within manufacturing tolerances and in response to reasonable loads applied thereto) or may include one or more portions configured to flex and/or articulate relative to a longitudinal axis thereof. A lumen 142 extends longitudinally through outer shaft 140. As also noted above, end effector assembly 150 is selectively movable relative to housing 110 and outer shaft 140 to enable deployment of end effector assembly 150 from outer shaft 140 from the retracted position (FIG. 1) to the deployed position (FIG. 2). More specifically, end effector assembly 150 is movable via drive shaft 185 between a retracted position (see FIG. 1), wherein end effector assembly 150 is disposed within lumen 142 defined in outer shaft 140, and a deployed position (FIG. 2), wherein at least a portion of end effector assembly 150 extends distally from outer shaft 140. Outer shaft 140, as noted above, may alternatively be slidable relative to housing 110 and end effector assembly 150 to enable selective deployment of end effector assembly 150 from outer shaft 140.

End effector assembly 150 includes a pair of arms 152, 154 and a tissue specimen bag 160 depending from arms 152, 154. Arms 152, 154 are configured for positioning within one or more channels 162, 164 formed about at least a portion of open end 166 of tissue specimen bag 160 to retain tissue specimen bag 160 on arms 152, 154. In the retracted position of end effector assembly 150, arms 152, 154 may be resiliently flexed inwardly to enable accommodation of arms 152, 154 within lumen 142 of outer shaft 140. Tissue specimen bag 160 may be furled, folded, or otherwise positioned in the retracted position of end effector assembly 150 to enable accommodation of tissue specimen bag 160 within lumen 142 of outer shaft 140. Upon deployment of end effector assembly 150 from outer shaft 140, arms 152, 154 are configured to resiliently return to a spaced-apart, curved configuration for retaining tissue specimen bag 160 thereon in an open condition, thus enabling insertion of a tissue specimen "T" (FIG. 6) through open end 166 of tissue specimen bag 160 and into the interior thereof. The resilient return of arms 152, 154 may also serve to unfold, unfurl, or otherwise manipulate tissue specimen bag 160 upon deployment from outer shaft 140.

Tissue specimen bag 160 may be formed from any suitable bio-compatible material (or materials), e.g., ripstop nylon, configured to retain a tissue specimen "T" (FIG. 6) therein. As noted above, tissue specimen bag 160 depends from arms 152, 154 in the deployed position of end effector assembly 150 such that articulation of arms 152, 154 likewise articulates tissue specimen bag 160. Tissue specimen bag 160 defines at least one opening, e.g., at open end 166 thereof, and includes one or more channels 162, 164 formed about open end 166 thereof for receipt of arms 152, 154, respectively, therein. The one or more channels 162, 164 may be separate or in communication with one another, and/or may extend about only a portion of open end 166 of tissue specimen bag 160 or about the entirety perimeter thereof. One or more of the openings of tissue specimen bag 160, e.g., open end 166, may include a cinch cord (not shown) disposed thereabout to enable selective closure of the opening. Tissue specimen bag 160 may be disengaged from arms 152, 154 upon cinching closed open end 166 of tissue specimen bag 160, retraction of end effector assembly 150 back towards the retracted position (FIG. 1), using a separate instrument, e.g., grasping device, and/or in any other suitable manner.

Figure 4A:
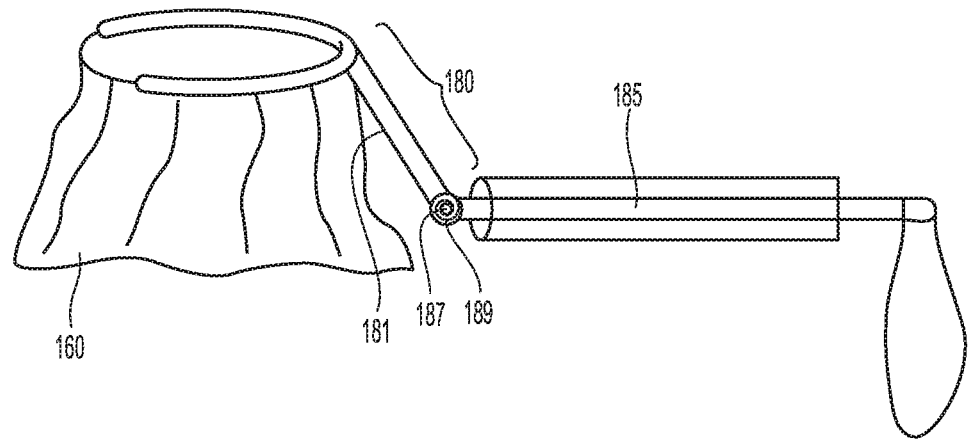
FIG. 4A is a side view of one embodiment of a tissue specimen retrieval device according to the present disclosure having an articulating linkage disposed at a distal end thereof.

With reference to FIG. 4A, one embodiment of an articulation portion 180 according the present disclosure is shown. More particularly, articulating element 180 is proximally disposed relative to arms 152, 154 and includes a link 181 pivotably coupled by pivot 187 to a distal end of the drive shaft 185 of end effector assembly 150. Link 181 is biased (via a torsion spring 189 or otherwise) to articulate the end effector assembly 150 once fully deployed from outer shaft 140 (See FIG. 4A). In other words, drive shaft 185 is initially actuated distally via retraction of actuator 120 to deploy end effector assembly 150 from outer shaft 140. When initially deployed (FIG. 2), at least a portion of link 181 remains within outer shaft 140 such that end effector assembly 150 remains in a generally parallel orientation with respect to outer shaft 140.

To enable articulation, a second actuator 130 is actuated to urge drive shaft 185 further distally to expose the entirety of link 181 from outer shaft 140. Once link 181 is fully exposed, the acting bias forces end effector assembly 150 to articulate to achieve the proper elevation to contain the tissue specimen within the specimen bag 160. The acting bias may be any type of biasing mechanism known in the art, e.g., torsion spring 189. Alternatively, first actuator 120 may be used for this purpose and second actuator 130 may be eliminated. More particularly, first actuator 120 may be configured to have multiple positions, e.g., a first position that urges drive shaft 185 distally to deploy the arms 152, 154 of end effector assembly 150 from shaft 140 and end effector assembly 150 to a parallel orientation relative to outer shaft 140 (FIG. 2) and a second position that urges drive shaft 185 further distally to expose link 181 to articulate the end effector assembly 150 relative to the outer shaft 140 (FIG. 4A).

Figure 4B:
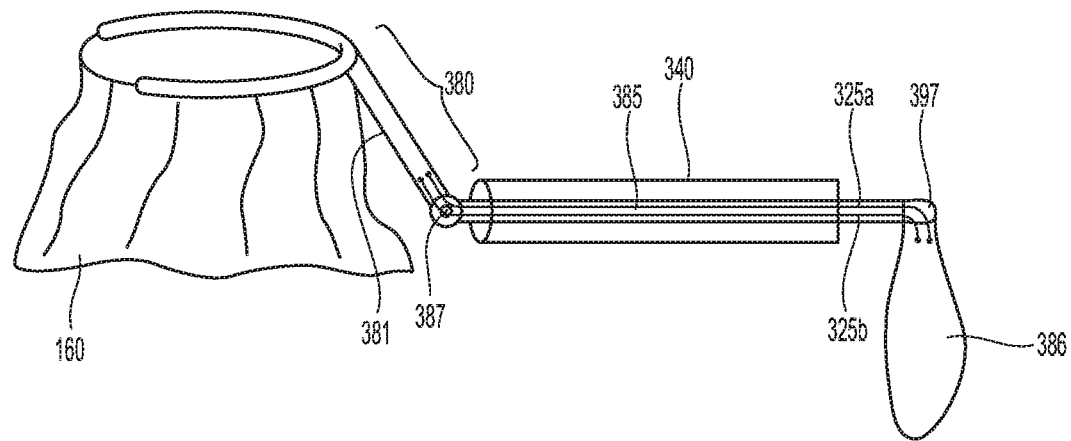
FIG. 4B is a side view of another embodiment of a tissue specimen retrieval device according to the present disclosure having an articulating linkage disposed at a distal end thereof

FIG. 4B shows another embodiment of tissue specimen retrieval device 300 according to the present disclosure. Device 300 includes a plurality of links, e.g., links 381, 385 and 386 which cooperate to articulate the articulating element 180 to allow the specimen bag 160 to engage tissue. Link 381 and link 385 are coupled via pivot 387 and link 385 and link 386 are coupled via pivot 397. Pivots 387 and 397 may be configured to allow movement from an aligned condition along an axis defined through outer shaft 340 in only one direction to a position such that portion 380 is articulated or angled relative to shaft 340. The direction of movement of the links 381 and 386 may be the same or opposite.

Cables 325*a* and 325*b* are attached at respective proximal and distal ends to links 381 and 386. By manipulating link 386 (which may include an actuator or which may be a moveable handle) in a first direction, tension is placed on one of the cables, e.g., cable 325*a*, and by manipulating the link 386 in a second direction, tension is place on the other cable, e.g., cable 325*b*. Moving link 386 to different positions causes consequent tension in either cable 325*a* or 325*b* which, since cables 325*a* and 325*b* are anchored to respective links 381 and 386 at both ends, articulates the distal portion 380 and bag 160 as needed.

Figure 5:
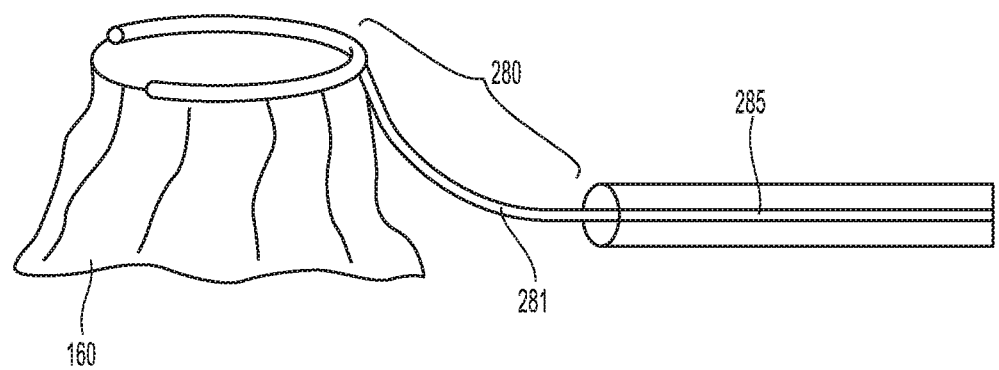
FIG. 5 is a side view of another embodiment of a tissue specimen retrieval device according to the present disclosure having an articulating shaft made at least partially from a shape memory allow.

FIG. 5 shows another embodiment of an articulation portion 280 according to the present disclosure. Portion 280 includes a drive shaft 285 (or, again, a drive shaft) that operably couples to actuator 120 to allow selective deployment of end effector assembly 150. More particularly, articulating element 280 is proximally disposed relative to arms 152, 154 and includes a resilient portion 281 disposed at a distal end of the drive shaft 285 of end effector assembly 150. Upon exposure of the resilient portion 281 from outer shaft 140, the end effector assembly 150 articulates under the force of the spring action of the resilient portion 281 to articulate the end effector assembly 150 to the proper elevation to contain the tissue specimen within the specimen bag 160.

In embodiments, drive shaft 285 may be initially actuated distally via retraction of actuator 120 to deploy end effector assembly 150 from outer shaft 140. When initially deployed (FIG. 2), at least a portion of the resilient portion 281 remains within outer shaft 140 such that end effector assembly 150 remains in a generally parallel orientation with respect to outer shaft 140. Alternatively, the resilient portion 281 may be configured longer to gradually articulate the end effector assembly 150 to the proper orientation for tissue retrieval as the resilient portion 281 is gradually exposed from outer shaft 140.

Second actuator 130 may be utilized and actuated to urge drive shaft 285 further distally to expose the entirety of resilient portion 281 from outer shaft 140. Once resilient portion 281 is fully exposed, the acting bias of the resilient portion 281 forces end effector assembly 150 to articulate to achieve the proper elevation to contain the tissue specimen within the specimen bag 160. Alternatively, first actuator 120 may be used for this purpose and second actuator 130 may be eliminated. More particularly, first actuator 120 may be configured to have multiple positions, e.g., a first position that urges drive shaft 285 to deploy the arms 152, 154 of end effector assembly 150 from shaft 140 such that end effector assembly 150 is parallel relative to outer shaft 140 (FIG. 2) and a second position that urges drive shaft 285 further distally to expose resilient portion 281 to articulate the end effector assembly 150 relative to the outer shaft 140 (FIG. 4A).

In embodiments, the resilient portion 281 may be made from a shape memory alloy. As the end effector assembly 150 is extended from the distal end of outer shaft 140, the end effector assembly 150 articulates to achieve the proper elevation to contain the tissue specimen. Shape memory alloys (SMAs) are a family of alloys having anthropomorphic qualities of memory and trainability and are particularly well suited for use with medical instruments. One of the most common SMAs is Nitinol which can retain shape memories for two different physical configurations and changes shape as a function of temperature. Other SMAs have been developed based on copper, zinc and aluminum and have similar shape memory retaining features which may be induced by temperature or in the present case stressed-induced conditions.

SMAs undergo a crystalline phase transition upon applied temperature and/or stress variations. A particularly useful attribute of SMAs is that after it is deformed by temperature/stress, it can completely recover its original shape on being returned to the original temperature. The ability of an alloy to possess shape memory is a result of the fact that the alloy undergoes a reversible transformation from an austenite state to a martensite state with a change in temperature (or, alternatively, a stress-induced condition as explained below). This transformation is referred to as a thermoelastic martensite transformation.

Under normal conditions, the thermoelastic martensite transformation occurs over a temperature range which varies with the composition of the alloy, itself, and the type of thermal-mechanical processing by which it was manufactured. In other words, the temperature at which a shape is "memorized" by an SMA is a function of the temperature at which the martensite and austenite crystals form in that particular alloy. For example, Nitinol alloys can be fabricated so that the shape memory effect will occur over a wide range of temperatures, e.g., −270° to +100° Celsius. If utilized with one or more of the embodiments described herein, the tissue retrieval device 100 and articulation portion 281 would need to include some sort of temperature regulator (not shown) to induce the SMA transformation.

As mentioned above, SMAs are also known to display stress-induced martensite (SIM) transformation which occurs when the alloy is deformed from its original austenite state to a martensite state by subjecting the alloy to a stress condition. For example and with respect to FIG. 5 of the present disclosure, articulating element 281 may be generally bent or arcuately-shaped when disposed in its original or austenite state (see FIG. 2). When articulating element 281 is positioned within outer shaft 140, articulating element 281 is deformed, i.e., straightened, into a stress-induced martensite state enabling the user to more easily navigate the articulating element 281 and outer shaft 140 through tight body cavities and passageways to access tissue. When the articulating element 281 is exposed to less or no stress (e.g., exposed from the outer shaft 140), the articulating element 281 automatically transforms to the austenite state (bent or arcuately-shaped) to achieve the proper elevation to contain the tissue specimen (FIG. 5). Once the tissue specimen is contained in the tissue specimen bag 160, the user may actuate one or both actuators (as described above) to retract the articulating element 281 back into the outer shaft 140.

In embodiments, a rotation knob (not shown) associated with housing 110 and operably coupled to end effector assembly 150 may be provided to enable selective rotation of end effector assembly 150 about the longitudinal axis of outer shaft 140 and relative to housing 110.

With reference to FIGS. 1-6, in use, end effector assembly 150 is initially disposed in the retracted position to facilitate insertion of the tissue specimen retrieval device 100 through an access cannula "C" (FIG. 6) or natural passageway into an internal body cavity "B" (FIG. 6). Actuator 120 is initially disposed in a distal-most position to maintain end effector assembly 150 and tissue specimen bag 160 within outer shaft 140. Once tissue specimen retrieval device 100 is disposed within the internal body cavity "B" (FIG. 6) as desired, and with reference to FIGS. 2, 4A, and 5, end effector assembly 150 is deployed from outer shaft 140 by actuating first actuator 120 from a more-distal position to a more-proximal position to thereby urge drive shaft 185, 285 distally such that end effector assembly 150 is deployed to the deployed position (FIG. 2). At this point, end effector assembly 150 remains aligned on the longitudinal axis of outer shaft 140.

If it is desired to articulate end effector assembly 150 relative to outer shaft 140 after end effector assembly 150 is deployed from outer shaft 140, second actuator 130 is moved proximally from a closer position relative to housing 110 to a further proximally-spaced position relative to housing 110 to thereby urge drive shaft 185, 285 further distally to articulate the end effector assembly 150 as described above. As mentioned above, first actuator 120 may be utilized to accomplish both deployment and articulation. For example, first actuator 120 may be actuated from a first position wherein the end effector assembly is disposed within outer shaft 140 to an intermediate position wherein the end effector assembly 150 is deployed and aligned with outer shaft 140 (FIG. 2). First actuator 120 is then selectively actuatable from the intermediate position to the second position to articulate the end effector assembly 150 as needed for tissue retrieval (FIGS. 4A and 5).

Although both actuator 120 and actuator 130 are shown as having an inverse or opposite actuation effect when actuated (e.g., proximal actuation yields distal advancement of drive shaft 185, 285), there may be a direct correlation between actuation of either actuator 120 or 130 and the actual actuation effect (e.g., distal actuation yields distal advancement of drive shaft 185, 285).

In embodiments, the arms 152, 154 may be spring biased such that, once deployed from the distal end of the outer shaft 140, the arms 152, 154 open to facilitate unfurling of the tissue specimen bag 160. In other embodiments, a lock (not shown) may be included with either or both actuating mechanisms 120, 130 to enable a user to lock the end effector assembly 150 in a deployed position for manipulation or lock the end effector assembly 150 in a particular articulated position. If a rotation mechanism is contemplated as mentioned above, a lock (not shown) may be utilized for this purpose as well. Any type of known locking mechanism is contemplated for this purpose.

Turning momentarily to FIG. 6, the above-detailed articulation of end effector assembly 150 of tissue specimen retrieval device 100 facilitates orientation of open end 166 of tissue specimen bag 160 in an appropriate position within the internal body cavity "B" to facilitate positioning of a tissue specimen "T" therein. End effector assembly 150 may be returned to the retracted position, which also serves to return end effector assembly 150 to the aligned position, by actuating second actuator 130 to move the drive shaft 185, 285 to generally align end effector assembly 150 with outer shaft 140. First actuator 120 is then actuated from the more-proximal position to the more-distal position to retract the end effector assembly 150 within outer shaft 140. As such, end effector assembly 150 is moved to the aligned position and returned to the retracted position to facilitate retrieval of end effector assembly 150 from the internal body cavity "B."

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue specimen retrieval device, comprising:
   a housing;
   an outer shaft extending distally from the housing and defining a longitudinal axis;
   an end effector assembly extending distally from the outer shaft in a deployed position of the end effector assembly;
   a first actuator operably associated with the housing and actuatable to deploy and retract the end effector assembly;
   a drive shaft operably coupled to the first actuator and including a link disposed at a distal end thereof that operably couples to the end effector assembly, the drive shaft movable via actuation of the first actuator between a first position wherein the end effector assembly and link are retracted within the outer shaft and a second position wherein the end effector assembly and link are fully exposed from the outer shaft, the link including a biasing member that, once the link is fully exposed, articulates the end effector assembly to a position to engage a tissue specimen, wherein the drive shaft is movable to an intermediate position between the first and second positions wherein the end effector assembly is fully exposed from the outer shaft while the link remains at least partially disposed within the outer shaft, and wherein, when disposed in the intermediate position, the end effector assembly remains parallel to the longitudinal axis of the outer shaft; and
   a second actuator operably coupled to the drive shaft, wherein the first actuator actuates the drive shaft to move between the first position and the intermediate position to expose the end effector assembly and the second actuator actuates the drive shaft to move between the intermediate position and the second position to expose the link and articulate the end effector assembly.

2. The tissue specimen retrieval device according to claim 1, wherein the end effector assembly includes first and second arms configured to support a tissue specimen bag thereon.

3. The tissue specimen retrieval device according to claim 1, wherein the first actuator is actuated in one direction from an un-actuated position to an actuated position and in an opposite direction from the actuated position back to the un-actuated position.

4. The tissue specimen retrieval device according to claim 1, wherein deployment of the end effector assembly automatically unfurls a tissue specimen bag.

5. A tissue specimen retrieval device, comprising:
   a housing;
   an outer shaft extending distally from the housing and defining a longitudinal axis;
   an end effector assembly extending distally from the outer shaft in a deployed position of the end effector assembly;
   a first actuator operably associated with the housing and actuatable to deploy and retract the end effector assembly;
   a drive shaft operably coupled to the first actuator and including a resilient portion having a bias disposed at a distal end thereof that operably couples to the end effector assembly, the drive shaft movable via actuation of the first actuator between a first position wherein the end effector assembly and resilient portion are retracted within the outer shaft and a second position wherein the end effector assembly and resilient portion are fully exposed from the outer shaft, the bias of the resilient portion articulating the end effector assembly to a position to engage tissue, wherein the drive shaft is movable to an intermediate position between the first and second positions wherein the end effector assembly is fully exposed from the outer shaft while the resilient portion remains at least partially disposed within the outer shaft, and wherein, when disposed in the intermediate position, the end effector assembly remains parallel to the longitudinal axis of the outer shaft; and
   a second actuator operably coupled to the drive shaft, and wherein the first actuator actuates the drive shaft to move between the first position and the intermediate position to expose the end effector assembly and the second actuator actuates the drive shaft to move between the intermediate position and the second position to expose the resilient portion and articulate the end effector assembly.

6. The tissue specimen retrieval device according to claim 5, wherein the end effector assembly includes first and second arms configured to support a tissue specimen bag thereon.

7. The tissue specimen retrieval device according to claim 5, wherein the first actuator is actuated in one direction from an un-actuated position to an actuated position and in an opposite direction from the actuated position back to the un-actuated position.

8. The tissue specimen retrieval device according to claim 5, wherein deployment of the end effector assembly automatically unfurls a tissue specimen bag.

9. The tissue specimen retrieval device according to claim 5, wherein the resilient portion is made from a shape memory alloy.

10. The tissue specimen retrieval device according to claim 9, wherein the shape memory alloy is thermoelastic to transform from an austenite, straight configuration to a martensite, arcuate configuration.

11. The tissue specimen retrieval device according to claim 9, wherein the shape memory alloy is stress-induced to transform from an austenite, straight configuration to a martensite, arcuate configuration.

* * * * *